United States Patent
Avidor et al.

(10) Patent No.: US 10,577,560 B2
(45) Date of Patent: Mar. 3, 2020

(54) GRASS SCENT FORMULATIONS AND USES THEREOF

(71) Applicant: Agan Aroma & fine chemicals Ltd., Ashdod (IL)

(72) Inventors: Yoav Avidor, Tel-Aviv (IL); Itsik Bar-Nahum, Kfar-Gibton (IL); Sasson Shemesh, Rehovot (IL)

(73) Assignee: Agan Aroma & fine chemicals Ltd., Ashdod (IL)

( * ) Notice: Subject to any disclaimer, the term of this patent is extended or adjusted under 35 U.S.C. 154(b) by 69 days.

(21) Appl. No.: 15/550,053

(22) PCT Filed: Feb. 11, 2016

(86) PCT No.: PCT/IL2016/050169
§ 371 (c)(1),
(2) Date: Aug. 10, 2017

(87) PCT Pub. No.: WO2016/128982
PCT Pub. Date: Aug. 18, 2016

(65) Prior Publication Data
US 2018/0016520 A1    Jan. 18, 2018

Related U.S. Application Data

(60) Provisional application No. 62/115,179, filed on Feb. 12, 2015.

(51) Int. Cl.
| | | |
|---|---|---|
| *C11B 9/00* | (2006.01) | |
| *E01C 13/08* | (2006.01) | |
| *A61K 8/9789* | (2017.01) | |
| *A61Q 13/00* | (2006.01) | |
| *A61K 8/34* | (2006.01) | |

(52) U.S. Cl.
CPC .............. *C11B 9/0015* (2013.01); *A61K 8/34* (2013.01); *A61K 8/9789* (2017.08); *A61Q 13/00* (2013.01); *C11B 9/00* (2013.01); *C11B 9/0019* (2013.01); *E01C 13/08* (2013.01)

(58) Field of Classification Search
CPC ..................................... C11B 9/0015
See application file for complete search history.

(56) References Cited

U.S. PATENT DOCUMENTS

| | | | |
|---|---|---|---|
| 4,613,457 A | 9/1986 | Bloesl et al. | |
| 6,976,451 B2 | 12/2005 | Helfman | |
| 2004/0022966 A1 | 2/2004 | Weder | |
| 2006/0040073 A1* | 2/2006 | Straughn | E01C 13/08 428/17 |
| 2008/0241371 A1 | 10/2008 | Havelka et al. | |
| 2009/0035488 A1 | 2/2009 | Astenius | |
| 2011/0104092 A1* | 5/2011 | Panten | C11B 9/0019 424/65 |
| 2012/0018528 A1* | 1/2012 | Samain | H04L 67/125 239/6 |

FOREIGN PATENT DOCUMENTS

| | | |
|---|---|---|
| JP | 2003-113392 | 4/2003 |
| WO | WO 2009/124888 | 10/2009 |
| WO | WO 2016/128982 | 8/2016 |

OTHER PUBLICATIONS

International Preliminary Report on Patentability dated Aug. 24, 2017 From the International Bureau of WIPO Re. Application No. PCT/I12016/050169. (1 Page).
International Search Report and the Written Opinion dated May 15, 2016 From the International Searching Authority Re. Application No. IL2016/050169.
Supplementary European Search Report and the European Search Opinion dated May 30, 2018 From the European Patent Office Re. Application No. 16748841.0. (7 Pages).
Notice of Reasons for Rejection dated Oct. 29, 2019 From the Japan Patent Office Re. Application No. 2017-542043 and Its Translation Into English. (9 Pages).

* cited by examiner

*Primary Examiner* — Arrie L Reuther

(57) ABSTRACT

A scenting concentrate and a formulation containing same, which imparts a long-lasting grass scent, is disclosed. Methods and systems utilizing the formulation for imparting a grass scent to a substrate such as artificial grass are also disclosed.

33 Claims, No Drawings

GRASS SCENT FORMULATIONS AND USES THEREOF

RELATED APPLICATIONS

This application is a National Phase of PCT Patent Application No. PCT/IL2016/050169 having International filing date of Feb. 11, 2016, which claims the benefit of priority under 35 USC § 119(e) of U.S. Provisional Patent Application No. 62/115,179 filed on Feb. 12, 2015. The contents of the above applications are all incorporated by reference as if fully set forth herein in their entirety.

FIELD AND BACKGROUND OF THE INVENTION

The present invention, in some embodiments thereof, relates to aroma-imparting formulations and, more particularly, but not exclusively, to grass-scented formulations and uses thereof for imparting a fresh-cut grass odor to synthetic or artificial grass.

Aroma-imparting (also referred to herein and in the art as fragrance-imparting, odor-imparting, flavor-imparting, aroma-inducing) agents are widely used in fields such beverages, cosmetics, sanitary and hygienic goods, detergents, bath refreshing additives, medicines, and agricultural chemicals. Aroma-imparting agents are used for imparting scent, odor, aroma or fragrance to the product.

A fragrance (or scent, odor, or aroma) results from a combination of a variety of components in a fragrance composition. Ordinarily, fragrances are created by blending materials (ingredients, components) such as odoriferous essential oils, botanic extracts, resins, animal secretions, and synthetic aromatic materials. These materials are blended in order to achieve what are known as "top note", "middle note" and "bottom note" components.

A "top note" is the quality perceived immediately upon application. A "base note" is the essence of the fragrance. It typically consists of of large, heavy molecules that evaporate slowly. Some base notes are perceived more than 24 hours after application. The "middle note" is the perceived quality that bridges from top to base note. It typically emerges after the top note.

In recent years, green note fragrance/aroma-imparting agents have been of particular interest in the field of perfumery. The fresh aroma of freshly cut green grass fragrance-imparting agents are used in candles, potpourri, bath and body products, melt-and-pour soap, cold process soap, gel wax, and the like.

Artificial grass (also referred to herein and in the art as "artificial turf" or "synthetic grass") was first marketed in the 1960's and was originally used in sports applications as an alternative to natural grass. The application and market for artificial grass have grown considerably ever since and currently involve several additional large business sectors including home landscaping, golf courses, pet areas, playground areas and the like.

The growing market for artificial grass has been driven mainly by the high cost of water and the need, and sometimes governmental requirement, to reduce irrigation in many areas in the world. Additional factors include allergies, and the need to control grass-related pesticides, which are associated with natural grass.

Significant advances have been made in the field of manufacturing and processing artificial grass that closely resembles natural grass in its look and feel. However, currently available artificial grasses are typically adversely characterized by a tendency to heat up, and in addition, lack a grass scent.

U.S. Patent Application Publication No. 2009/0035488 teaches a synthetic grass comprising a scenting ingredient that emits fresh cut grass scent, being layered in the synthetic grass or incorporated within the polymeric materials composing the synthetic grass.

U.S. Patent Application Publication No. 2006/0040073 teaches artificial turf which resembles natural grass and is transportable, and which may comprise strands treated with an aroma inducing agent that imparts grass scent.

Additional background art includes U.S. Pat. No. 6,976,451, U.S. Patent Application Publication Nos. 2004/0022966 and 2008/0241371.

SUMMARY OF THE INVENTION

According to an aspect of some embodiments of the present invention there is provided a scenting concentrate comprising: cis-3-hexenol at a concentration of at least 5 weight percents of the total weight of the concentrate; an ester of cis-3-hexenol having an evaporation number higher than 50 (a "heavy" ester, as described herein), at a concentration of at least 5 weight percents of the total weight of the concentrate; Galbanum resinoid at a concentration of at least 3 weight percent of the total weight of the concentrate; and an alcoholic carrier comprising at least one alcohol characterized by one or more of: a boiling temperature higher than 300° C.; substantivity of at least 300 hours; and evaporation number higher than 50, relative to diethyl ether.

According to some of any of the embodiments of the present invention, the concentrate is characterized by a long-lasting grass scent.

According to some of any of the embodiments of the present invention, a concentration of the cis-3-hexenol is at least 10 weight percents.

According to some of any of the embodiments of the present invention, a concentration of the cis-3-hexenol ranges from 10 to 20 weight percents.

According to some of any of the embodiments of the present invention, a concentration of the ("heavy") ester of cis-3-hexenol having an evaporation number higher than 50 is at least 10 weight percents.

According to some of any of the embodiments of the present invention, a concentration of the ("heavy") ester of cis-3-hexenol having an evaporation number higher than 50 ranges from 10 to 20 weight percents.

According to some of any of the embodiments of the present invention, the ("heavy") ester of cis-3-hexenol imparts a base note of a grass scent (e.g., has the corresponding substantivity).

According to some of any of the embodiments of the present invention, the ("heavy") ester of cis-3-hexenol, having evaporation number higher than 50, is cis-3-hexenyl salicylate.

According to some of any of the embodiments of the present invention, a concentration of the galbanum resinoid is at least 3 weight percents.

According to some of any of the embodiments of the present invention, a concentration of the galbanum resinoid ranges from 5 to 6 weight percents.

According to some of any of the embodiments of the present invention, a concentration of the alcoholic carrier is at least 30 weight percents of the total weight of the concentrate.

According to some of any of the embodiments of the present invention, the concentrate further comprises atralone.

According to some of any of the embodiments of the present invention, a concentration of the atralone ranges from 1 to 2 weights percents.

According to some of any of the embodiments of the present invention, the concentrate further comprises at least one additional odoriferous material that imparts a grass scent.

According to some of any of the embodiments of the present invention, the additional odoriferous material imparts a top note of the grass scent (e.g., has an evaporation number lower than 15 or lower than 10 and/or low substantivity, as described herein).

According to some of any of the embodiments of the present invention, a concentration of the at least one additional odoriferous material ranges from 1 to 20 weight percents, or from 5 to 15 weight percents of the total weight of the composition.

According to some of any of the embodiments of the present invention, the at least one additional odoriferous material that imparts a grass scent is selected from the group consisting of trans-3-hexenol, trans-2-hexenal, trans-2-hexenol, cis-2-hexenol, 1-hexanol, 1-hexanal, cis-3-hexenal, and an ester of cis-3-hexenol having an evaporation number lower than 15 or lower than 10.

According to some of any of the embodiments of the present invention, the at least one additional odoriferous material that imparts a grass scent is selected from the group consisting of trans-3-hexenol, trans-2-hexenal, trans-2-hexenol, 1-hexanol, and an ester of cis-3-hexenol having an evaporation number lower than 15 or lower than 10 (and/or low substantivity, as described herein).

According to some of any of the embodiments of the present invention, the ester of cis-3-hexenol is selected from the group consisting of cis-3-hexenyl acetate, cis-3-hexenyl formate and cis-3-hexenyl-isobutyrate (verdural).

According to some of any of the embodiments of the present invention, the concentrate further comprises an odoriferous material that imparts a ligneous hay odor.

According to some of any of the embodiments of the present invention, the odoriferous material imparts a base note of the ligneous hay odor (substantivity higher than 100 hours, or 200 hours and/or evaporation number higher than 50).

According to some of any of the embodiments of the present invention, a concentration of the odoriferous material that imparts a ligneous hay odor ranges from 2 to 10, or from 3 to 7, weight percents of the total weight of the concentrate.

According to some of any of the embodiments of the present invention, the odoriferous material is selected from the group consisting of cedarwood oil Virginia and isobornyl cyclohexanol.

According to some of any of the embodiments of the present invention, the concentrate further comprises an odoriferous material that imparts a top note of a fresh scent.

According to some of any of the embodiments of the present invention, a concentration of the odoriferous material that imparts a top note of a fresh scent ranges from 1 to 10, or from 2 to 6, weight percents of the total weight of the concentrate.

According to some of any of the embodiments of the present invention, the odoriferous material that imparts a top note of a fresh scent is selected from the group consisting of Dihydromyrcenol, Linalyle Acetate, Styrallyl Acetate.

According to some of any of the embodiments of the present invention, the concentrate further comprises an odoriferous material that imparts a green or floral base note (e.g., characterized by substantivity higher than 200 hours and/or evaporation number higher than 50).

According to some of any of the embodiments of the present invention, a concentration of the odoriferous material ranges from 0.5 to 5 weight percents of the total weight of the composition.

According to some of any of the embodiments of the present invention, the odoriferous substance is selected from the group consisting of Dupical, Adoxal, Lilial, and Trans-2-cis-6-Nonadienal.

According to some of any of the embodiments of the present invention, the concentrate further comprises an odoriferous material that imparts a herbal hay odor.

According to some of any of the embodiments of the present invention, a concentration of the odoriferous material that imparts a herbal hay odor ranges from 1 to 10 weight percents of the total weight of the composition.

According to an aspect of some embodiments of the present invention there is provided a scenting formulation comprising the concentrate as described herein in any of the respective embodiments and any combination thereof, mixed with a liquid carrier.

According to some of any of the embodiments of the present invention, the liquid carrier comprises an alcohol, water or a mixture thereof.

According to some of any of the embodiments of the present invention, the liquid carrier comprises ethanol.

According to some of any of the embodiments of the present invention, a concentration of the concentrate in the formulation ranges from 1 to 50 weight percents of the total weight of the formulation.

According to some of any of the embodiments of the present invention, the concentration ranges from 5 to 15 weight percents.

According to an aspect of some embodiments of the present invention there is provided a scenting formulation comprising the concentrate as described herein in any of the respective embodiments and any combination thereof and a solid matrix.

According to some of any of the embodiments of the present invention, the scenting formulation is in a form of capsules, granules, beads, pellets, and the likes.

According to an aspect of some embodiments of the present invention there is provided a kit comprising the concentrate or the formulation as described herein in any of the respective embodiments and any combination thereof.

According to some of any of the embodiments of the present invention, the kit further comprises means for applying the concentrate or the formulation to a substrate.

According to an aspect of some embodiments of the present invention there is provided a concentrate, a formulation or a kit, as described herein in any of the respective embodiments and any combination thereof, for use in a method of imparting a grass scent to a substrate.

According to some of any of the embodiments of the present invention, the method is effected by periodically contacting the substrate with the formulation as described herein in any of the respective embodiments and any combination thereof.

According to some of any of the embodiments of the present invention, the contacting is effected within periodic intervals of at least 3 days.

According to some of any of the embodiments of the present invention, the contacting is effected by spraying or dispensing the formulation on the substrate.

According to some of any of the embodiments of the present invention, the contacting is effected by irrigation.

According to some of any of the embodiments of the present invention, the substrate is artificial grass.

According to an aspect of some embodiments of the present invention there is provided a system for imparting a grass scent to a substrate, the system being configured to periodically apply the formulation as described herein in any of the respective embodiments and any combination thereof to the substrate.

According to some of any of the embodiments of the present invention, the system is configured to apply the formulation to the substrate within periodic intervals of at least 3 days.

According to some of any of the embodiments of the present invention, the system is a computerized system.

According to some of any of the embodiments of the present invention, the substrate is an artificial grass.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

DESCRIPTION OF SPECIFIC EMBODIMENTS OF THE INVENTION

The present invention, in some embodiments thereof, relates to aroma-imparting formulations and, more particularly, but not exclusively, to grass-scented formulations and uses thereof for imparting a fresh-cut grass odor to substrates such as artificial grass.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Embodiments of the present invention relate to a scenting base formulation (concentrate) and a solid or liquid formulation containing same, which is aimed to provide an odor of a natural grass to artificial grass, other artificial green plants and grass-related artificial products, and also to natural plants.

The formulation disclosed herein meets a long felt need in the field of artificial grasses and grass-related artificial products, as it imparts a long-lasting grass scent to the artificial grass or product. More specifically, the formulation disclosed herein imparts a grass scent that remains for at least 2 days, preferably for at least 3 days, at least 4 days, and even for at least 5 days or more. The formulation provided herein is chemically stable to environmental conditions (e.g., irrigation, precipitations), that is, its aroma-imparting (scenting) effect remains when a substrate (e.g., artificial grass) to which it is applied is subjected to such conditions.

The formulation provided herein is readily and cost-efficiently applied to large areas such as public lands, fields, yards or courts, as well as to private, small areas such as private gardens or yards. The formulation provided herein is also characterized as non-irritating and non-toxic to plants and animals (including humans).

The scenting concentrate in the formulation provided herein comprises cis-3-hexenol (also known as cis-3-hexen-1-ol, and mainly as "leaf alcohol") as the main scenting ingredient that imparts a fresh grass scent. However, as cis-3-hexenol is a volatile compound, and features relatively low evaporation number and substantivity, the present inventors have devised and successfully prepared and practiced a concentrate and a formulation containing same, which comprise additional components that contribute to maintaining the fresh grass scent for a period of at least 48 hours. Herein throughout, the term "concentrate" is also referred to as "a base formulation" and describes a concentrated formulation which comprises cis-3-hexenol and additional ingredients that provide a long-lasting scenting effect.

The term "formulation", as used herein throughout, describes a diluted form of the base formulation, which is the final product that is applied to a substrate as defined herein.

By "scenting" is it meant, herein throughout, imparting a scent.

The term "scent" is also referred to herein interchangeably as aroma, or fragrance or odor.

By "long-lasting scenting effect" it is meant imparting a scent for a period longer than a few hours, namely, longer than 24 hours, 37 hours, 48 hours, 60 hours, 72 hours, 84 hours, 96 hours, and even longer than 100 hours.

Herein throughout, some substances used for forming the concentrate as described herein are categorized by imparting a top note, a base note or a middle note, as these terms are known and referred to in the art.

Some substances are categorized interchangeably by their volatility and/or substantivity. The volatility of substances can be determined by e.g., boiling point and/or evaporation number.

It is to be noted that according to the present embodiments, some substances are defined by a characteristic volatility (e.g., the note type, the boiling point and/or the evaporation number) and/or by substantivity, and that these substances are to be considered per one of these characteristics or per a combination of these characteristics.

The term "substantivity" is used herein and in the art of fragrances and perfumes to describe the persistence of a fragrant on the substrate to which it is applied. This term is typically reflected by the time period from application of a substance to a substrate during which the scent imparted by the substance persists, while considering conditions such as removal of the vehicle, contact with water, friction and the like. Values of substantivity provided in the art usually refer to a skin substrate, and consider also conditions to which the skin substrate is subjected to, such as sweating, swimming, bathing and the like. Substantivity of ingredients in a scenting formulation can be calculated according to methods known in the art and/or which can be found in public databases. Reference is made, for example, to www(dot)thegoodscentscompany(dot)com/data; Manuel Zarzo, Sensors, 2013, 13(1):463-483; and "Flavor, Fragrance and Odor analysis", Ed. Ray Marsilli, CRC Press, 29 Nov. 2001". Base notes typically have substantivity higher than 100 hours. Middle notes typically have substantivity of 10-100. Top notes typically have substantivity lower than 10.

The term "evaporation number" as used herein and in the art, describes measurable values for empirically determining volatility of substances. The evaporation number (En) describes the evaporation time of a liquid substance compared to a standard liquid, for which En is determined as 1. Measurements of En are typically performed typically at a temperature of 293±2 K, and a relative atmospheric humidity of 65%±5% during measurement. En can be determined using standard assays, such as described in DIN 53249; 1995-01. In some assays, the standard is diethyl ether for which En is 1.

Highly volatile substances (e.g., which impart a top note as defined herein) have En lower than 10; moderately volatile substances (e.g., which impart a middle note as defined herein) have En of from 10 to 35, substances of low volatility have En of from 35 to 50, and very low volatile substances have an En higher than 50. Substances of low and very low volatility typically impart a base note, as defined herein.

The evaporation numbers referred to herein are relative to diethyl ether, and are measurable by, or in accordance with, standard assays such as DIN assays or ISO assays.

According to an aspect of some embodiments of the present invention there is provided a scenting concentrate (a base formulation) comprising cis-3-hexenol, an ester of cis-3-hexenol which is characterized by high substantivity and/or high evaporation number, Galbanum resinoid, and alcoholic carrier.

According to some of any of the embodiments of the present invention, cis-3-hexenol is present in the base formulation at a concentration of at least 5 weight percents of the total weight of the concentrate, and in some embodiments, cis-3-hexenol is present in the base formulation at a concentration of at least 5 weight percents of the total weight of the concentrate. In some embodiments, a concentration of cis-3-hexenol in the base formulation ranges from 5 to 30 weight percents, or from 10 to 20 weight percents or from 10 to 15 percents or from 12 to 20, or from 15 to 20 weight percents, including any subrange or intermediate value therebetween.

According to some of any of the embodiments of the present invention, the ester of cis-3-hexenol is a "heavy" ester of cis-3-hexenol, characterized by high substantivity and/or high evaporation number. In some embodiments, the ester of cis-3-hexenol is characterized by substantivity higher than 100 hours, 150 hours or 200 hours. Due to its high substantivity, such a "heavy" ester imparts a base note of the formulation, for example, a green, floral or grass scent base note.

Alternatively or additionally, the "heavy" ester of cis-3-hexenol is characterized as having an evaporation number higher than 50, or higher than 60, or even higher than 70. Alternatively or additionally, the ester of cis-3-hexenol is characterized by a boiling temperature higher than 200° C., 250° C. or even higher 300° C.

According to some of any of the embodiments of the present invention, a concentration the "heavy" ester of cis-3-hexenol is at least 5 weight percents of the total weight of the concentrate, or at least 10 weight percents of the total weight of the composition. In some embodiments is in the range of from 10 to 20 weight percents or from 10 to 15 weight percents; or from 12 to 16 weight percents.

An exemplary "heavy" ester of cis-3-hexenol is cis-3-hexenyl salicylate.

According to some of any of the embodiments of the present invention, additional "heavy" substances are included in the base formulation, for imparting a long-lasting scenting effect. These substances are characterized by substantivity higher than 100 hours, or higher than 200 hours, and even higher than 300 hours, and/or by evaporation number that is higher than 50, higher than 60 or higher than 70 (or from 35 to 100 or from 50 to 100). In some embodiments, such ingredients are present in the base formulation at a concentration ranging from 1 to 10 weight percents in total, or 3 to 7 weight percents in total.

An exemplary such ingredient is Galbanum resinoide, which is also known as *ferula galbaniflua* resinoid [CAS NO. 9000-24-2], and which is the extraction of the Galbanum Gum found in the roots of the umbelliferous wild plant called *Ferula Galbaniflua* (grown in Iran and Afghanistan).

Galbanum Resinoid can be present in the base formulation at a concentration ranging from 3 to 7 weight percents, or from 5 to 7, or from 5 to 6 weight percents.

In some of any of the embodiments described herein, the base formulation comprises an alcoholic substance at a concentration of at least 30 weight percents, or ranging from 30 to 40 weight percents, which is also referred to herein as an alcoholic carrier or an alcoholic base.

In some embodiments the alcoholic base comprises one or more "heavy alcohols" characterized by substantivity higher than 100 hours, or higher than 200 hours or preferably higher than 300 hours, and/or by evaporation number higher than 60, higher than 70 or higher (or of from 50 to 100). Alternatively or additionally, the one or more "heavy alcohol" is characterized by a boiling temperature higher than 300° C.

Exemplary alcoholic substances that may form the alcoholic base of the base formulation include, but are not limited to, tri- or tetra-alkyleneglycols, such as tetraethylene glycol, or tetrapropylene glycol, or higher alkylene glycols, tricyclodecane methylol (TCDM) and/or ester or ether derivatives thereof, tricyclodecane dimethylol (TCD DM) or ester or ether derivatives thereof, isobornyl cyclohexanol, and methyl abietate [CAS No. 127-25-3] and/or derivatives thereof.

Exemplary alcoholic substances that are usable in the context of these embodiments of the present invention are described, for example, in U.S. Pat. No. 4,123,394, and/or can be represented by the general Formula:

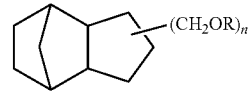

wherein n can be an integer of from 1 to 6, preferably, 1-3, preferably 2; and

R is hydrogen, alkyl, alkenyl, alkynyl and/or acyl, as these terms are defined herein.

In some embodiments, the alcoholic base comprises one or more of a "heavy" alcohol as described herein and additional one or more substances commonly used as carriers of odor formulations. Exemplary such substances include, but are not limited to, Benzyl Benzoate (BB) [CAS No. 120-51-4], Diethyl Phthalate (DEP) [CAS No. 84-66-2], Dipropylene Glycol (DPG) [CAS No. 2526571-8], Isopropyl Myristate (IPM) [CAS No. 110-27-0], and Triethyl Citrate (TIC) [CAS No. 77-93-0].

According to some of any of the embodiments described herein, the base formulation further comprises, as a substance of high substantivity and/or high evaporation number, a mossy ingredient such as oak moss.

Oak moss is also known as Atralone or Evernyl or "Mousse de Maitre", or as methyl 2,4-dihydroxy-3,6-dimethyl-benzoate; CAS No. 4707-47-5.

Atralone can be present in the base formulation at a concentration ranging from 0.1 to 3 weight percents, or from 1 to 3, or from 1 to 2 weight percents.

In some of any one of the embodiments described herein, the base formulation further comprises additional ingredients (fragrances), including one or more of an odoriferous material that imparts a grass scent, an odoriferous material that imparts a ligneous hay odor, an odoriferous material that imparts a top note of a fresh scent, an odoriferous material that imparts a green or floral base note, and/or an odoriferous material that imparts a herbal hay odor.

According to some embodiments, the base formulation further comprises at least one odoriferous material that imparts a grass scent, in addition to the cis-3-hexenol.

In some embodiments, such an odoriferous material is characterized by moderate to low substantivity (e.g., lower than 100 hours, or lower than 24 hours or lower than 10 hours), and/or moderate to low evaporation number (e.g., lower than 35, lower than 15, or lower than 10) and hence is aimed at imparting a top note of a grass scent.

Exemplary such odoriferous materials include, but are not limited to, trans-3-hexenol (the conformational isomer of cis-3-hexenol), trans-2-hexenal (also known as "Leaf aldehyde"), trans-2-hexenol, cis-2-hexenol, 1-hexanol, 1-hexanal, cis-3-hexenal, and an ester of cis-3-hexenol characterized by low substantivity and/or by low evaporation number (high volatility), as described herein.

Exemplary esters of cis-3-hexenol suitable for use in the context of these embodiments include, but are not limited to, cis-3-hexenyl acetate, cis-3-hexenyl formate and cis-3-hexenyl-isobutyrate (verdural).

In some embodiments, the additional odoriferous materials that impart a top note of grass scent include one or more of trans-3-hexenol, trans-2-hexenal, trans-2-hexenol, 1-hexanol, and an ester of cis-3-hexenol as defined for these embodiments, and in some embodiments, the additional odoriferous materials that impart a top note of grass scent include all of the above.

In some embodiments, a total concentration of such one or more odoriferous materials ranges from 1 to 20 weight percents, or from 5 to 15 weight percents of the total weight of the composition, including any intermediate values and subranges therebetween.

According to some of any of the embodiments described herein, the base formulation further comprises one or more odoriferous materials that impart a ligneous hay odor.

In some embodiments, these materials are selected to impart a base note of a ligneous hay odor, and are characterized by high substantivity (e.g., higher than 100) and/or high evaporation number (e.g., higher than 50), as defined herein.

Exemplary such odoriferous materials include, but are not limited to, cedarwood oil Virginia and isobornyl cyclohexanol.

In some embodiments, the total concentration of such odoriferous materials is in a range of from 2 to 10, or 3 to 7, weight percents of the total weight of the concentrate.

According to some embodiments of the present invention, the base formulation further comprises an odoriferous material that imparts a top note of a fresh scent.

Exemplary such odoriferous materials are aldehydes and alcohols of moderate to low substantivity (e.g., lower than 100 hours, or lower than 24 hours, or lower than 10 hours) and/or moderate to low evaporation number (e.g., lower than 35, or lower than 15, or lower than 10), such as, but not limited to, Dihydromyrcenol, Linalyle Acetate, and Styrallyl Acetate. In some embodiments, the formulation comprises one or more, or all of such odoriferous materials.

In some embodiments, the total concentration of odoriferous materials that impart a top note of a fresh scent ranges from 1 to 10, or from 2 to 6, weight percents of the total weight of the concentrate.

According to some embodiments, the base formulation further comprises one or more odoriferous material selected to impart a green or floral base note.

In some embodiments, such odoriferous material are characterized by a high substantivity, as defined herein and/or by high evaporation number (e.g., higher than 50), as defined herein.

Exemplary such odoriferous materials include, but are not limited to, "heavy" aldehydes such as Dupical, Adoxal, Lilial, and Trans-2-cis-6-Nonadienal.

In some embodiments, one or more of the above aldehydes are included in the formulation, and in some embodiments, all of the above aldehydes are included in the formulation.

In some embodiments, a total concentration "heavy" odoriferous materials that impart a green or floral base note ranges from 0.5 to 5 weight percents of the total weight of the composition.

In some embodiments, the formulation comprises one or more additional odoriferous or other materials, such as aromatic oils and other plant extracts, aromatic esters, aromatic alcohols, and odoriferous materials that impart a herbal hay odor.

Exemplary such additional ingredients are listed in Table 1 hereinbelow, which presents exemplary, non-limiting formulations according to some embodiments of the present invention.

The base formulation, or concentrate, as described herein can be used for forming a final scenting formulation, upon being mixed with a carrier or vehicle.

According to an aspect of some embodiments of the present invention there is provided a scenting formulation comprising the concentrate as described herein.

In some embodiments, the formulation comprises a liquid vehicle with which the concentrate is mixed (diluted).

In some embodiments, such a carrier comprises an alcohol, water or an aqueous alcoholic solution.

In some embodiments, the carrier comprises from 10 to 100, or from 50 to 100 percents alcohol such as ethanol.

In some embodiments, the carrier consists of an alcohol such as ethanol.

In some embodiments, the final formulation comprises the concentrate at a concentration that ranges from 1 to 50 weight percents of the total weight of the formulation, or from 5 to 50, or from 5 to 20, or from 5 to 15 or from 10 to 20 weight percents of the total weight of the formulation.

In some embodiments, the final formulation is a solid formulation and the vehicle is a solid matrix.

In some embodiments, the concentrate is encapsulated within the solid matrix. Any matrix suitable for encapsulating the concentrate is usable in the context of these embodiments. The solid matrix can be selected to release the concentrate by immediate release mechanism, for example, upon rupturing, or by slow release mechanism, by diffusion, or by degradation.

The final form of a solid formulation can be, for example, capsules, granules, beads, pellets, and the like.

Exemplary solid formulations are described, for example, in U.S. Patent Application Publication Nos. 2009/0035488 and 2005/0153135, which are incorporated by reference as if fully set forth herein.

In some of any of the embodiments described herein, the final formulation is provided per se. Alternatively, a kit is provided, for preparing and/or employing the final formulation.

In some embodiments, the kit comprises the liquid final formulation as described herein.

In some embodiments, the kit comprises the concentrate and instructions to mix the concentrate with a liquid vehicle as described herein.

In some embodiments, the kit comprises the concentrate and the liquid vehicle, packaged separately, and instructions to mix the concentrate and the vehicle at appropriate amounts, to achieve a concentration of the concentrate as described herein.

In some embodiments, the kit comprises a solid formulation as described herein, and instructions how to dispense the solid formulation. Alternatively, the kit comprises means for dispensing the formulation.

In some embodiments, the kit further comprises means for dispensing any of the formulations described herein, for example, a spraying bottle and other devices or systems as is further detailed hereinunder.

In some of any of the embodiments described herein for a kit, the kit further comprises instructions to use the formulation as described herein, by applying it to a substrate by a method as described herein, in any of its respective embodiments and any combination thereof.

According to an aspect of some embodiments of the present invention, any of the concentrates, formulations and kits, as described in any one of the respective embodiments, is for use in a method of imparting a grass scent to a substrate.

The substrate can be, for example, artificial grass, including decorative grass, or any other artificial green plant and artificial grass-related product, or natural green plants, such as natural vegetation (e.g., natural grass, natural groundcover, etc.), as well as any other natural or artificial plants.

Any commercially available or otherwise publicly available artificial grass or other substrates are contemplated. The artificial grass can be, for example, of public playgrounds, sport yards, home yards, and the likes.

In some embodiments, the method described herein is considered as treating a substrate, such as artificial grass, as described herein.

In some embodiments the method is effected by periodically contacting the substrate with, or applying to the substrate, a formulation as described herein in any of the respective embodiments and any combination thereof.

By "periodically" it is meant repeatedly contacting the substrate with the formulation, or repeatedly applying the formulation to the substrate, within repeated time intervals.

In some embodiments, the contacting is effected within periodic intervals of 3 days or more, e.g., every 3 days, or every 4 days, or even every 5 days.

Contacting the substrate with a formulation as described herein can be made by any technique for applying or dispensing liquid or solid formulations onto substrates, such as, but not limited to, spraying or dispensing the formulation and/or irrigating the substrate.

The following lists some non-limiting techniques suitable for applying a formulation as described herein onto substrates (or for contacting a substrate with the formulation).

In one exemplary embodiment, contacting or applying is effected by means of spraying.

A non-limiting example of a device for spraying the formulation onto a substrate is a hand-held container (e.g., bottle-shaped) equipped with a spray nozzle, and filled with the formulation. The device can be equipped with a hand-operated trigger or valve, which, when operated, dispenses the formulation through the spray nozzle. Alternatively or additionally, the device can include means for connecting the spray nozzle to a pressure source (e.g., a fluid source, such as, but not limited to, a source of pressurized water or air), such that the formulation is dispensed from the container through the spray nozzle by means of the pressure applied by the pressure source.

Such hand-held devices can form a part of a kit as described herein. For example, a container filled with the formulation, and equipped with the spray nozzle can be packaged within the kit, accompanied by instructions to operate the spray nozzle by the hand-operated trigger or by connecting it to a pressure source.

Alternatively, spraying can be effected by passing the liquid formulation through the spray nozzle by means of a pump. Devices as described herein, which further comprise such a pump are therefore also contemplated. Wheeled machines having means for dispensing the liquid formulation through one or more spray nozzles, as a result of a pressure supplied by a pump, and also usable in the context of these embodiments.

Distribution of the liquid formulation can also be effected by means of a propeller, optionally connected to a pump.

Also contemplated are devices and systems for dispensing solid formulations on small and large areas. Wheeled machines having means for dispensing granules, pellets or beads are usable to this effect, for example. Any device, machine or system for dispensing granular chemicals, which is used, for example, for lawn treatment, is contemplated.

Also contemplated are systems deployed for distributing liquid or solid formulation on relatively large areas (e.g., at least 10 square meters). Such a system can comprise a controller, a liquid or solid distribution system and a communication channel or network establishing communication between the controller and the distribution system. The controller optionally and preferably includes an electronic circuit configured for operating the distribution system.

As discussed hereinabove, due to the long-lasting scenting effect provided by the formulations described herein, applying the formulation to a substrate can be effected by periodic intervals of 3 days or more. Any of the methods, systems and devices described herein can therefore be employed in accordance with these time intervals. Thus, for example, a controller in an exemplary system as described herein can operate the distribution system at periodic intervals of 3 days or more. The system also comprises a data processor which can be configured to vary the time intervals employed by the controller based on a predetermined criterion or set of criteria.

The distribution system can be, for example, a liquid distribution system such as, but not limited to, a lawn sprinkler system, a center-pivot irrigation system, a drip irrigation system, a mist sprayer system, and the like.

It is expected that during the life of a patent maturing from this application many relevant technologies for distributing liquid and solid formulation over an area will be developed and the scope of the term liquid distribution system is intended to include all such new technologies a priori.

It is also expected that during the life of a patent maturing from this application many relevant artificial grasses will be developed and the scope of the term artificial grass is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The term "alkyl" describes a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms (C(1-4) alkyl).

Alkene and Alkyne, as used herein, are an alkyl, as defined herein, which contains one or more double bond or triple bond, respectively.

The term "acyl" as used herein, describes a —C(=O)—R' group, wherein R' can be hydrogen, alkyl, alkenyl or alkynyl, as defined herein.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Material and Methods

All ingredients were purchased from known vendors, such as Agan Aroma & Fine Chemicals, Givaudan, Firmenich, Negev Aroma and others.

Base formulations were prepared by mixing all ingredients at room temperature.

Final formulation were prepared by diluting a base formulation with an alcoholic carrier (e.g., ethanol or a mixture of ethanol and water), at a ratio of at least 1:1, preferably from 1:5 to 1:10.

Exemplary final formulations contained 10-20% by weight of the base formulation and 80-90% ethanol, respectively.

Example 1

Exemplary Base Formulations

Exemplary base Formulations were prepared by mixing at room temperature the ingredients listed in Table 1:

TABLE 1

| Ingredient | CAS# | % wt. (range) | % wt. (exemplary) I | % wt. (exemplary) II |
|---|---|---|---|---|
| Dupical | 30168-23-1 | 0.01-0.20% | 0.09% | 0.10% |
| Adoxal | 141-13-9 | 0.01-0.30% | 0.18% | 0.10% |
| Verdural B (cis-3-hexenyl isobutyrate) | 41519-23-7 | 0.1-0.3% | 0.18% | 0.20% |
| Fir Balsam AB | 8024-15-5 | 0.1-0.3% | 0.27% | 0.20% |
| Geraniol 98% | | 0.0-0.5% | 0.27% | — |
| cis-3-Hexenyl Formate | 33467-73-1 | 0.1-1.0% | 0.36% | 0.40% |
| Lilial OU (Lysmeral) | | 0.0-1.0% | 0.45% | — |
| Trans-2-cis-6-Nonadienal 10% DPG | 557-48-2 | 0.1-1.0% | 0.55% | 0.30% |
| Isoamyl Salicylate | 87-20-7 | 0.1-1.0% | 0.55% | 0.30% |

TABLE 1-continued

| Ingredient | CAS# | % wt. (range) | % wt. (exemplary) I | % wt. (exemplary) II |
|---|---|---|---|---|
| Acetate DBMC | | 0.0-1.0% | 0.55% | — |
| Allyl amyl Glycolate | 67634-00-8 | 0.1-1.0% | 0.64% | 0.50% |
| Trans-2-Hexenal | 6728-26-3 | 0.5-1.5% | 0.91% | 1.10% |
| cis-3-Hexenyl Acetate | 3681-71-8 | 0.5-1.5% | 0.91% | 0.80% |
| Trans-2-Hexenol | 928-95-0 | 0.1-5.0% | 1.00% | 3.50% |
| Styrallyl Acetate | 93-92-5 | 0.5-2.0% | 1.27% | 1.00% |
| Trans-3-Hexenol | 928-97-2 | 1.0-5.0% | 1.27% | 3.00% |
| Dimethylbenzyl Carbinol | 100-86-7 | 0.1-2.0% | 1.36% | 0.50% |
| Linalool | 78-70-6 | 0.5-2.0% | 1.36% | 1.00% |
| Triplal | 68039-49-6 | 0.5-2.0% | 1.36% | 1.00% |
| Atralone | 4707-47-5 | 1.0-2.0% | 1.73% | 1.20% |
| Dihydromyrcenol | 18479-58-8 | 1.0-3.0% | 2.09% | 1.50% |
| 1-Hexanol | 111-27-3 | 2.0-3.0% | 2.27% | 2.50% |
| Lyral | 31906-04-4 | 0.1-5% | 2.27% | 1.00% |
| Phenylethyl Alcohol | 60-12-8 | 1.0-3.0% | 2.55% | 1.50% |
| Linalyl Acetate | 115-95-7 | 1.0-5.0% | 2.73% | 2.00% |
| Cedarwood oil Virginia | 85085-41-2 | 2.0-3.0% | 2.73% | 2.50% |
| Isobornyl cyclohexanol | 3407-42-9 | 2.0-4.0% | 3.00% | 3.00% |
| Galbanum Resinoid | 8023-91-4 | 3.0-7.0% | 5.91% | 5.00% |
| cis-3-Hexenol | 928-96-1 | 10.0-20.0% | 11.36% | 16.00% |
| cis-3-Hexenyl Salicylate | 65405-77-8 | 10.0-20.0% | 12.73% | 14.00% |
| Additional odoriferous ingredients | | 2.0-6.0% | 4-5% | 3-4% |
| Alcoholic carrier | | Balance | balance | balance |
| | | | 100% | 100% |

Exemplary base Formulations I and II are provided herein as exemplary, non-limiting and non-representative base formulations. In Formulation II, the concentration of some of the ingredients that impart a grass scent, for example, cis-3-hexenol and trans-2-hexenol, was increased compared to Formulation I.

Example 2

An exemplary base formulation containing the ingredients listed in Table 1 above, at the indicated concentration ranges, was diluted in ethanol to form a 10% formulation, and the latter was applied onto an area of 30 cm×50 cm of artificial grass.

The grass scent was recognized well after more than 80 hours from the type the diluted formation was applied, and even for more than 90 hours and more than 120 hours, indicating a successful lost-lasting scenting effect of the formulation when applied to artificial grass.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A scenting concentrate comprising:
cis-3-hexenol at a concentration of at least 5 weight percent of the total weight of the concentrate;
an ester of cis-3-hexenol characterized by an evaporation number higher than 50, at a concentration of at least 5 weight percent of the total weight of the concentrate;
Galbanum resinoid at a concentration of at least 3 weight percent of the total weight of the concentrate; and
an alcoholic carrier comprising at least one alcohol characterized by:
a boiling temperature higher than 300° C.; and/or
substantivity of at least 300 hours; and/or
evaporation number higher than 50, relative to diethyl ether,
the scenting concentrate being characterized by a long-lasting grass scent.

2. The scenting concentrate of claim 1, wherein a concentration of cis-3-hexenol is at least 10 weight percent.

3. The scenting concentrate of claim 1, wherein a concentration of cis-3-hexenol ranges from 10 to 20 weight percent.

4. The scenting concentrate of claim 1, wherein a concentration of said ester of cis-3-hexenol having an evaporation number higher than 50 is at least 10 weight percent.

5. The scenting concentrate of claim 1, wherein a concentration of said ester of cis-3-hexenol characterized by an evaporation number higher than 50 ranges from 10 to 20 weight percent.

6. The scenting concentrate of claim 1, wherein said ester of cis-3-hexenol characterized by an evaporation number higher than 50 is cis-3-hexenyl salicylate.

7. The scenting concentrate of claim 1, wherein a concentration of said galbanum resinoid is at least 3 weight percent.

8. The scenting concentrate of claim 1, wherein a concentration of said galbanum resinoid ranges from 5 to 6 weight percent.

9. The scenting concentrate of claim 1, wherein a concentration of said alcoholic carrier is at least 30 weight percent of the total weight of the concentrate.

10. The scenting concentrate of claim 1, wherein:
a concentration of cis-3-hexenol is at least 10 weight percent;
a concentration of said ester of cis-3-hexenol having an evaporation number higher than 50 is at least 10 weight percent;
a concentration of said galbanum resinoid is at least 3 weight percent; and
a concentration of said alcoholic carrier is at least 30 weight percent of the total weight of the concentrate.

11. The scenting concentrate of claim 10, further comprising at least one of:
methyl 2,4-dihydroxy-3,6-dimethyl-benzoate;
an additional odoriferous material that imparts a top note of said grass scent and is characterized by an evaporation number lower than 15 or lower than 10;
an odoriferous material that imparts a ligneous hay odor, optionally a base note of said ligneous hay odor; optionally characterized by: substantivity higher than 100 hours; and/or an evaporation number higher than 50;
an odoriferous material that imparts a top note of a fresh scent;
an odoriferous material that imparts a green or floral base note, optionally characterized by substantivity higher than 200 hours; and/or evaporation number higher than 50; and
an odoriferous material that imparts a herbal hay odor.

12. The scenting concentrate of claim 11, wherein said at least one additional odoriferous material that imparts a grass scent is selected from the group consisting of trans-3-hexenol, trans-2-hexenal, trans-2-hexenol, cis-2-hexenol, 1-hexanol, 1-hexanal, cis-3-hexenal, and an ester of cis-3-hexenol characterized by an evaporation number lower than 15 or lower than 10.

13. The scenting concentrate of claim 12, wherein said ester of cis-3-hexenol is selected from the group consisting of cis-3-hexenyl acetate, cis-3-hexenyl formate and cis-3-hexenyl-isobutyrate (verdural).

14. The scenting concentrate of claim 11, wherein said odoriferous material that imparts a ligneous hay odor is selected from the group consisting of cedarwood oil Virginia and isobornyl cyclohexanol.

15. The scenting concentrate of claim 11, wherein said odoriferous material that imparts a top note of a fresh scent is selected from the group consisting of Dihydromyrcenol, Linalyl Acetate, Styrallyl Acetate.

16. The scenting concentrate of claim 11, wherein said odoriferous substance that imparts a top note of a fresh scent is selected from the group consisting of 4-(octahydro-4,7-methano-5H-inden-5-ylidene)butanal, 2,6,10-trimethylundec-9-enal, 3-(4-tert-butylphenyl)butanal, and Trans-2-cis-6-Nonadienal.

17. The scenting concentrate of claim 1, further comprising at least one of:
methyl 2,4-dihydroxy-3,6-dimethyl-benzoate;
an additional odoriferous material that imparts a top note of said grass scent and is characterized by an evaporation number lower than 15 or lower than 10;
an odoriferous material that imparts a ligneous hay odor, optionally a base note of said ligneous hay odor; optionally characterized by: substantivity higher than 100 hours; and/or an evaporation number higher than 50;
an odoriferous material that imparts a top note of a fresh scent;
an odoriferous material that imparts a green or floral base note, optionally characterized by substantivity higher than 200 hours; and/or evaporation number higher than 50; and an odoriferous material that imparts a herbal hay odor.

18. The scenting concentrate of claim 17, wherein said at least one additional odoriferous material that imparts a grass scent is selected from the group consisting of trans-3-hexenol, trans-2-hexenal, trans-2-hexenol, cis-2-hexenol, 1-hexanol, 1-hexanal, cis-3-hexenal, and an ester of cis-3-hexenol characterized by an evaporation number lower than 15 or lower than 10.

19. The scenting concentrate of claim 18, wherein said ester of cis-3-hexenol is selected from the group consisting of cis-3-hexenyl acetate, cis-3-hexenyl formate and cis-3-hexenyl-isobutyrate (verdural).

20. The scenting concentrate of claim 17, wherein said odoriferous material that imparts a ligneous hay odor is selected from the group consisting of cedarwood oil Virginia and isobornyl cyclohexanol.

21. The scenting concentrate of claim 17, wherein said odoriferous material that imparts a green or floral base note is selected from the group consisting of Dihydromyrcenol, Linalyl Acetate, Styrallyl Acetate.

22. The scenting concentrate of claim 17, wherein said odoriferous substance that imparts a green or floral base note is selected from the group consisting of 4-(octahydro-4,7-methano-5H-inden-5-ylidene)butanal, 2,6,10-trimethylundec-9-enal, 3-(4-tert-butylphenyl)butanal and Trans-2-cis-6-Nonadienal.

23. A scenting formulation comprising the scenting concentrate of claim 1 and a liquid carrier or a solid matrix.

24. The scenting formulation of claim 23, wherein a concentration of said concentrate in the formulation ranges from 1 to 50, or from 5 to 15, weight percent of the total weight of the formulation.

25. A kit comprising the scenting formulation of claim 23.

26. The kit of claim 25, further comprising means for applying the scenting formulation to a substrate.

27. A method of imparting a grass scent to a substrate, the method comprising periodically contacting the substrate with the scenting formulation of claim 23.

28. The method of claim 27, wherein said contacting is effected within periodic intervals of at least 3 days.

29. The method of claim 27, wherein said substrate is artificial grass.

30. A system for imparting a grass scent to a substrate, the system being configured to periodically apply the scenting formulation of claim 23 to the substrate.

31. The system of claim 30, being a computerized system.

32. The system of claim 30, wherein said substrate is an artificial grass.

33. A kit comprising the scenting concentrate of claim 1.

* * * * *